United States Patent
Aaron

(10) Patent No.: US 6,863,679 B1
(45) Date of Patent: Mar. 8, 2005

(54) PAIRED FORCEPS

(76) Inventor: William Stephen Aaron, 3313 Buffalo Trail, Floyds Knobs, IN (US) 47119

( * ) Notice: Subject to any disclaimer, the term of this patent is extended or adjusted under 35 U.S.C. 154(b) by 329 days.

(21) Appl. No.: 10/073,766

(22) Filed: Feb. 11, 2002

Related U.S. Application Data

(60) Provisional application No. 60/285,734, filed on Apr. 23, 2001.

(51) Int. Cl.[7] .............................................. A61B 17/50
(52) U.S. Cl. ........................ 606/210; 606/206; 606/207
(58) Field of Search ................................ 606/205, 206, 606/207, 208, 209, 210

(56) References Cited

U.S. PATENT DOCUMENTS

| | | | |
|---|---|---|---|
| 789,539 A | 5/1905 | Harris | |
| 2,214,984 A | 9/1940 | Bachmann | |
| 2,685,880 A | 8/1954 | Curutchet | |
| 4,318,313 A | 3/1982 | Tartaglia | |
| 4,462,404 A | 7/1984 | Schwarz et al. | |
| 4,950,281 A | 8/1990 | Kirsch et al. | |
| 5,449,374 A | * 9/1995 | Dunn et al. | 606/208 |
| 5,520,704 A | * 5/1996 | Castro et al. | 606/208 |
| 5,565,004 A | 10/1996 | Christoudias | |
| 5,980,534 A | * 11/1999 | Gimpelson | 606/119 |
| 6,106,542 A | 8/2000 | Toybin et al. | |

FOREIGN PATENT DOCUMENTS

WO    WO 98 49949 A    11/1998

* cited by examiner

*Primary Examiner*—Charles H. Sam
(74) *Attorney, Agent, or Firm*—Camoriano and Associates; Theresa Fritz Camoriano

(57) ABSTRACT

Two pairs of forceps, each pair having an inner leg and an outer leg, are connected together so that a surgeon can insert a forefinger between the inner legs of the two pairs and operate both pairs of forceps with one hand.

12 Claims, 6 Drawing Sheets

PAIRED FORCEPS

BACKGROUND OF THE INVENTION

The present invention relates to forceps, and, in particular, to two sets of forceps that are paired together to permit one person to perform a function that usually requires two people, each holding a forceps.

When a surgeon is performing surgery and is joining two adjacent edges of tissue together, the surgeon usually grasps one tissue with a pair of forceps and, in the other hand, holds a stapler or other joining device. The surgeon depends upon an assistant with a second pair of forceps to grasp the second tissue in order to bring the two tissues together, and the surgeon then staples or otherwise joins the tissues. Any type of tissue may be involved, such as skin, blood vessel walls, or visceral edges.

It has been recognized in the prior art that it would be desirable to devise a mechanism that would permit the surgeon to join the two edges of tissue together using only one hand, leaving the other hand free to hold a stapler, needle driver, or other device for securing the tissue edges together. Simultaneous elevation of the edges so grasped would obtain an eversion of the tissue edges that are coapted, a desired consequence in tissue closure. However, the prior art devices of which we are aware are difficult to use with any precision and are unfamiliar to the surgical hand.

SUMMARY OF THE INVENTION

The present invention provides a device that permits a surgeon to grasp two adjacent edges of tissue and draw them together using just one hand. This device uses two pairs of forceps that are attached together in such a way that the surgeon can insert his finger down between the two pairs in order to have good control of both pairs. The index finger lying between the two forceps can provide oppositional pressure in two directions at once, and it permits the surgeon to use intuitive skills to bring the tissue edges together.

DESCRIPTION OF THE PREFERRED EMBODIMENTS

Figure 1:
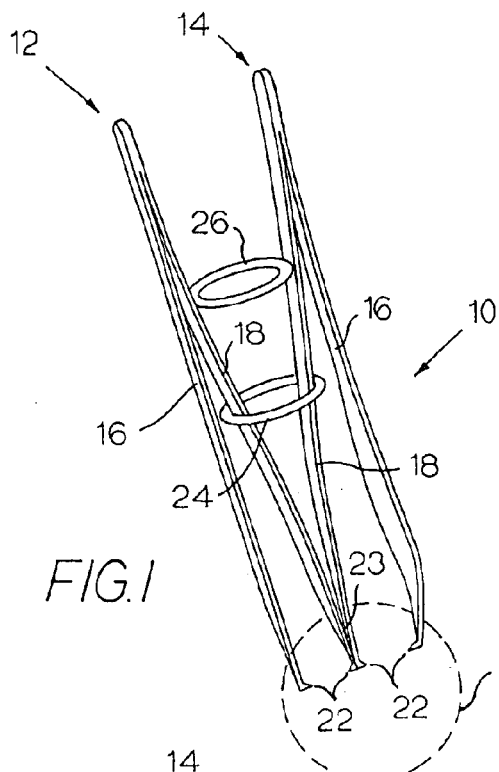
FIG. 1 is a perspective view of a first embodiment of a gripping device made in accordance with the present invention.

FIGS. 1–7 show a first embodiment of a gripping device 10 made in accordance with the present invention. The device 10 includes two pairs of forceps 12, 14, each made in a traditional way. Each pair of forceps 12, 14 includes first and second legs 16, 18 joined together at a hinge joint 20 at one end and having pointed gripping tips 22 at the other end. While this embodiment shows one type of gripping tip 22, many different types of gripping tips are known in the art and could be used, depending upon the type of tissue being joined. Similarly, while this embodiment shows one type of hinge joint 20, other types of hinge joints are also known and could be used. The hinge joint 20 restricts the relative motion between the inner and outer legs 18, 16 to motion within a plane.

Figure 2:
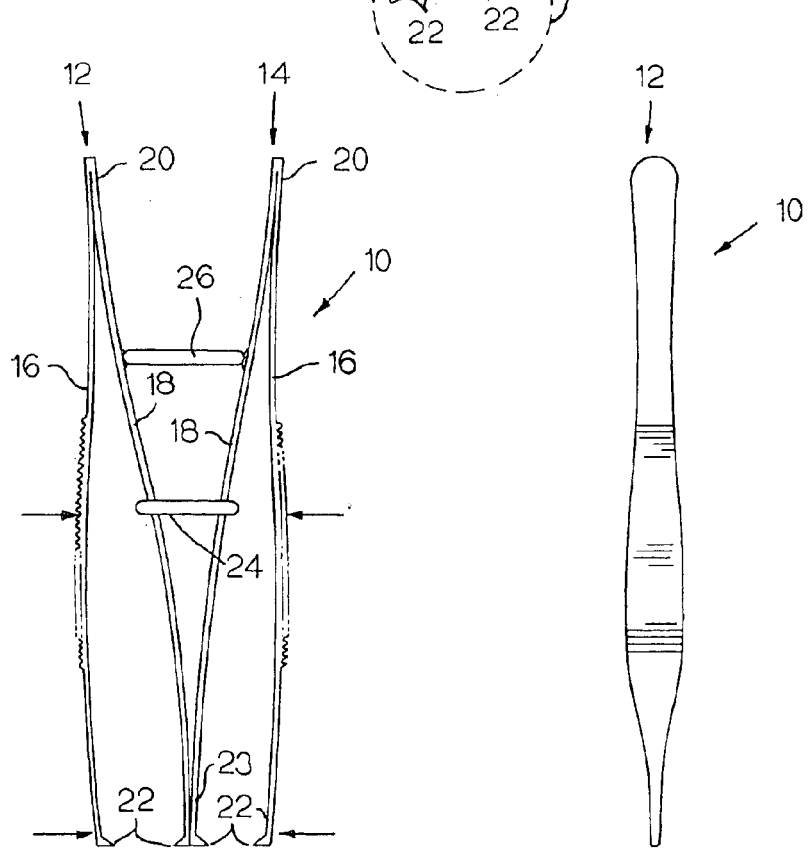
FIG. 2 is a front view of the gripping device of FIG. 1.
Figure 3:
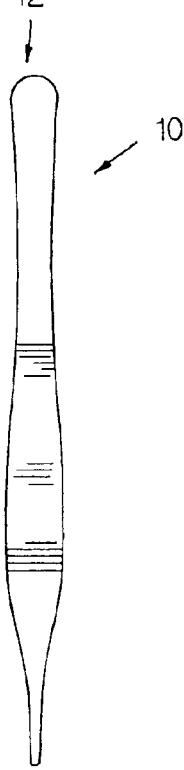
FIG. 3 is a side view of the gripping device of FIG. 1.
Figure 4:
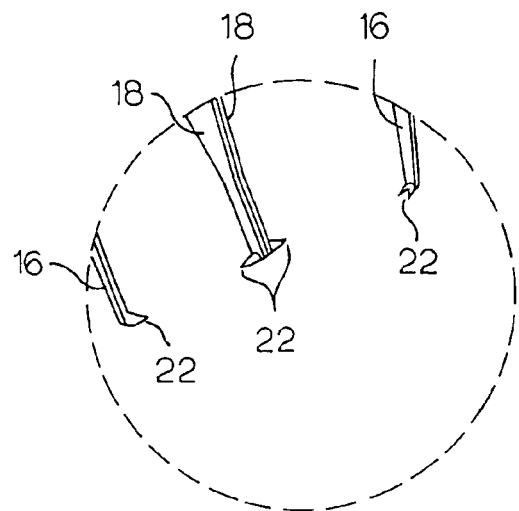
FIG. 4 is an enlarged view of the tip portion of the gripping device of FIG. 1.
Figure 5:
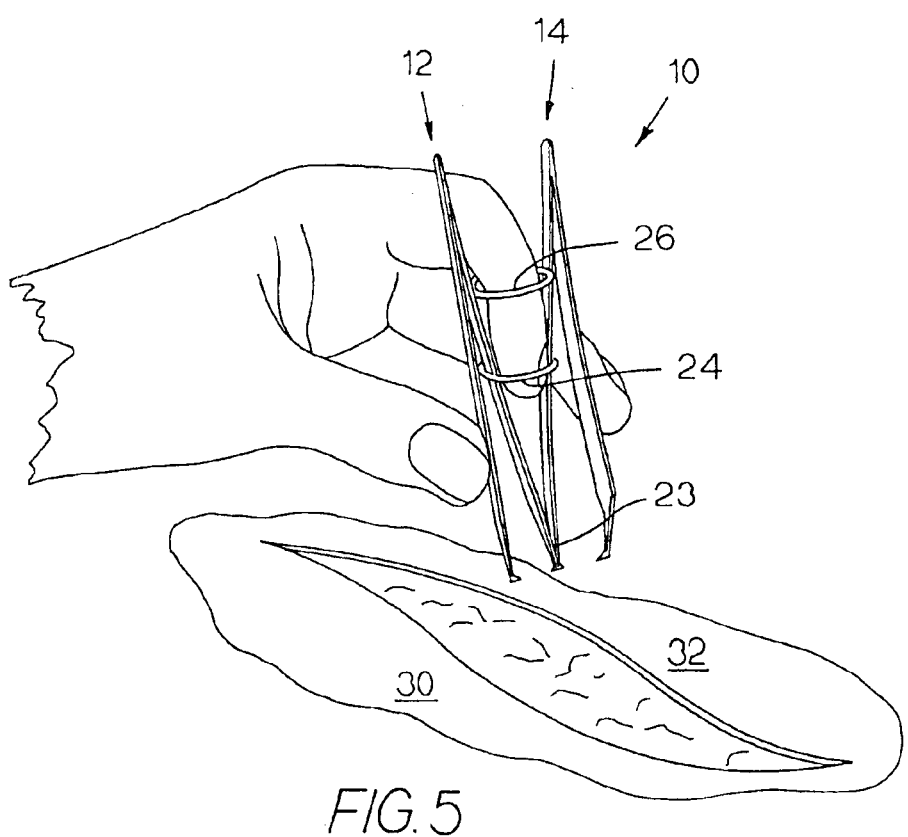
FIG. 5 is a perspective view showing the gripping device of FIG. 1 in use.

FIG. 2 has arrows showing the direction of relative motion of the legs, and, in this view, the plane of motion for both pairs of forceps is the plane of the paper. The outer legs 16 are moved inwardly toward the inner legs (or, if an outer leg 16 is stationary, its respective inner leg 18 may move outwardly toward the outer leg), moving along the plane of the paper, until the gripping tips 22 come together to grip the tissue.

The legs 16, 18 are made of a spring material, so that a fore is required to press the legs 16, 18 together in order to bring the tips 22 together, and, when that force is released, the legs 16, 18 return to their initial position, with the tips 22 separated as shown in FIG. 2.

The inner legs 18 of the two pairs of forceps 12, 14 are joined at the connection point 23, adjacent to their second (or gripping) end. While this connection point 23 is preferred, it is possible for the legs to be rigid enough that they do not have to be connected at their tips as long as they are joined together somewhere. They are also joined above the connection point 23 by two substantially rigid rings 24, 26, which function as spacers, holding the upper portions of the inner legs 18 above the connection 23 a fixed distance apart. (Other embodiments use other types of spacers, such as a spiral.) The first ring 24, lying closer to the connection 23, preferably has a smaller diameter than the second ring 26 in order to conform to the shape of the forceps. Also, in this preferred embodiment, the first ring surrounds the inner legs 18, while the second ring lies between the inner legs 18. In this preferred embodiment, the connection 23 is formed by welding, and the rings 24, 26 are welded to the inner legs 18. However, many other known connecting mechanisms could be used, including bolting, riveting, and forming as a unitary piece, for example. Both the connection 23 and the rings 24, 26 control the relative positions of the two pairs of forceps so that both pairs operate in the same plane of motion.

In order to use the gripping mechanism 10, the surgeon inserts a forefinger through the rings 24, 26 and puts a thumb against one of the outer legs 16 and another finger (preferably the middle finger) against the other of the outer legs 16. By adjusting the pressure between the fingers, the surgeon can control the amount of gripping force that is applied by each of the forceps 12, 14.

Figure 6:
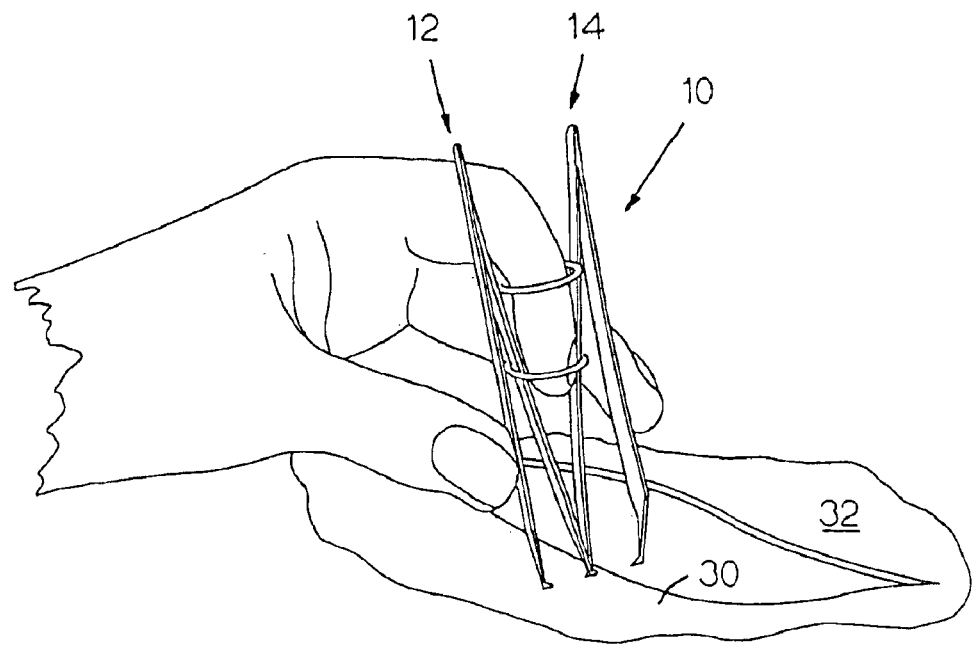
FIG. 6 is the same view as FIG. 5, showing the gripping device gripping a first edge of tissue.
Figure 7:
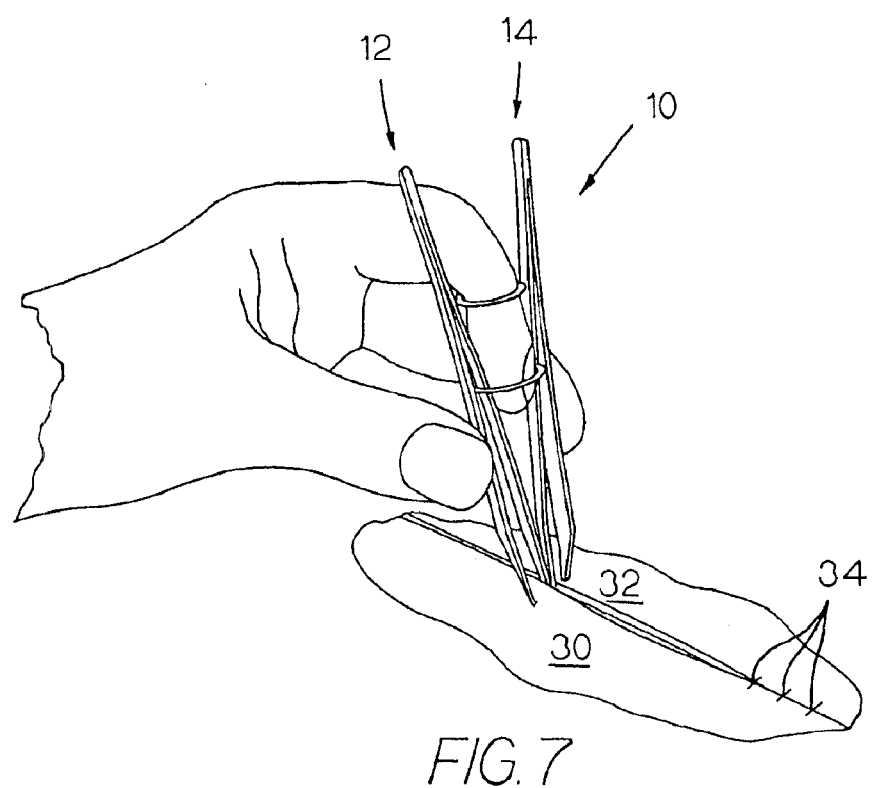
FIG. 7 is the same view as FIG. 6, but showing the gripping device gripping the second edge of tissue and bringing it together with the first edge, and showing some staples in place to secure the tissue edges together.

Typically, the surgeon will first grip a first edge of tissue 30 with the first pair of forceps 12 held between the forefinger and thumb, as shown in FIG. 6. Then, the surgeon will move the device 10 toward the second edge of tissue 32 and pick up that tissue edge with the second pair of forceps 14, thus holding the two tissue edges 30, 32 together with the two adjacent pairs of forceps 12, 14. The surgeon's other hand will then be free to apply staples 34, sutures (not shown) or other connectors to hold the tissue edges together.

While it is not absolutely necessary to have the rings 24, 26, and the gripper could function without them, it is preferred to have some type of substantially rigid spacer holding the upper portions of the inner legs 18 apart a fixed distance. If there were no spacer, the surgeon would have to use his forefinger to apply force in both directions at the same time in order to keep the upper portions of the legs 18 apart. With the spacer in place, holding either one of the upper leg portions of the inner legs 18 in position automatically positions the upper portion of the other inner leg 18. Thus, it is easier to use the device if some type of upper spacer is present than if a spacer is not present.

Figure 8:
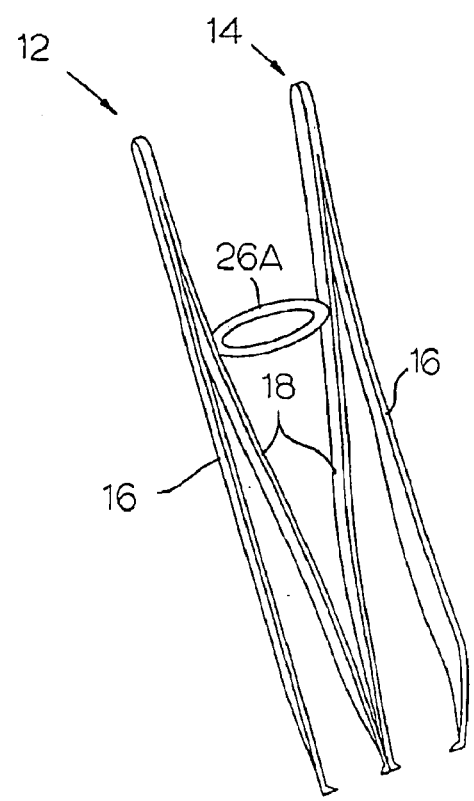
FIG. 8 is a perspective view of a second embodiment of a gripping device made in accordance with the present invention.
Figure 8A:
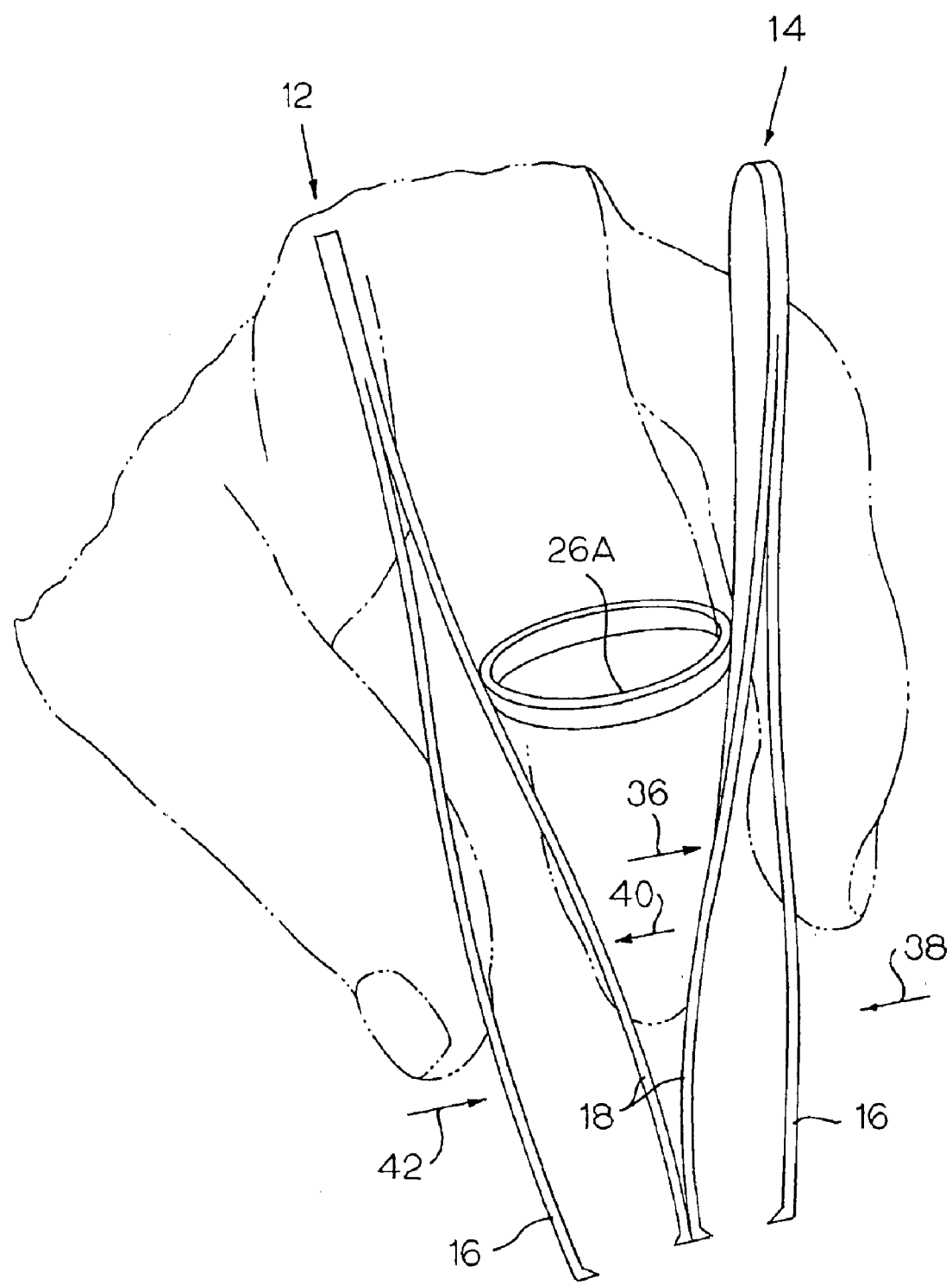
FIG. 8A shows the gripping device of FIG. 8 in use.

While the first embodiment shows the use of two rings 24, 26, other spacing arrangements could be used. For example, FIGS. 8 and 8A show the use of just a single ring 26A. The arrows 36, 38, 40, 42 in FIG. 8A show the positions and the directions in which force is applied. The index finger can actually apply force in two directions at once, as shown by the arrows 36, 40, to independently control the force applied by the two pairs of forceps 12, 14.

Figure 9:
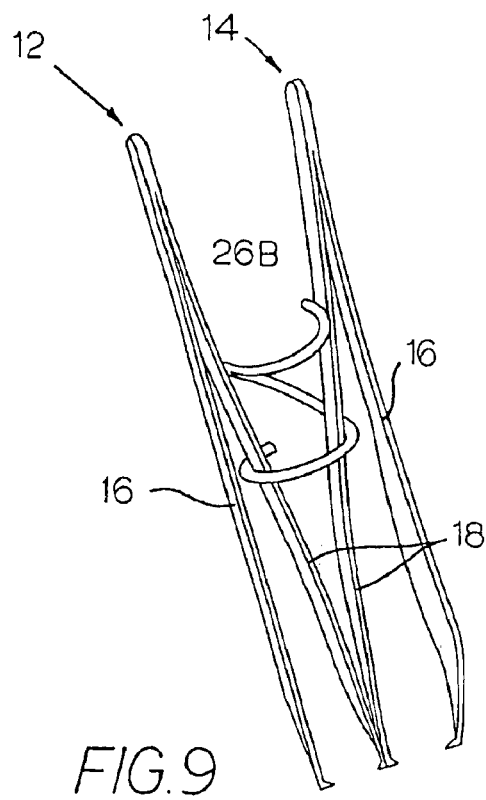
FIG. 9 is a perspective view of a third embodiment of a is gripping device made in accordance with the present invention.
Figure 11:
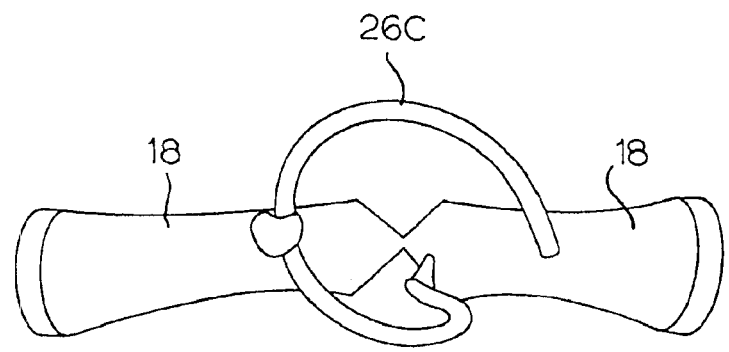
FIG. 11 is a top view of the gripping device of FIG. 10.
Figure 10:
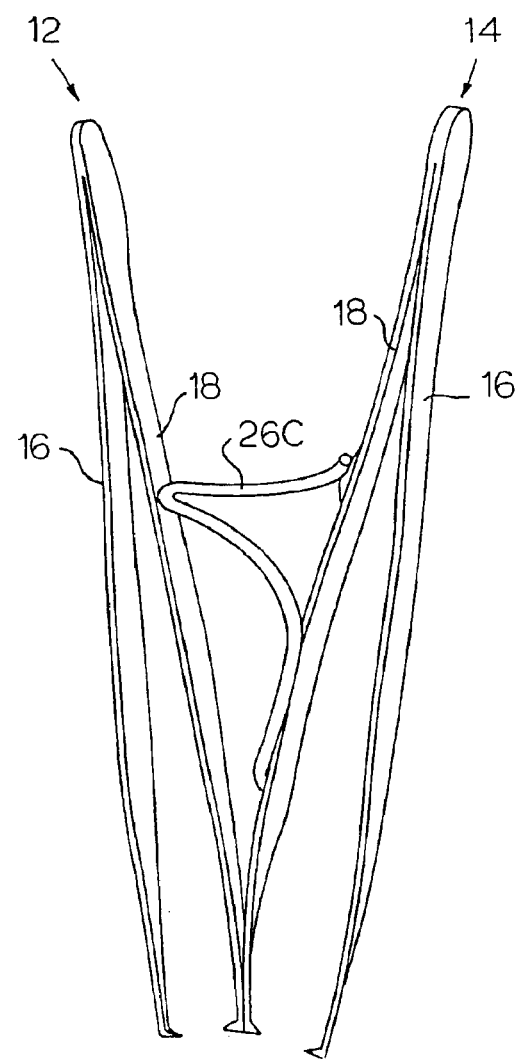
FIG. 10 is a perspective view of a fourth embodiment of a gripping device made in accordance with the present invention.

FIG. 9 shows the use of an S-shaped connector 26B. FIGS. 10 and 11 show an alternative spacer 26C, which is essentially the same as the S-shaped spacer 26B of FIG. 9, but with the lower portion removed. Each of the spacers 26–26C defines an opening, which permits the surgeon to insert a forefinger down between the two inner legs 18 of the gripper. The ability to insert the forefinger down between the inner legs 18 gives the surgeon far greater control over the gripper than would be possible if the forefinger could not be inserted between the inner legs 18.

It will be obvious to those skilled in the art that many modifications may be made to the embodiments described above without departing from the scope of the present invention.

What is claimed is:

1. A gripper, comprising:
   first and second pairs of forceps, each pair of forceps including an inner leg and an outer leg, each leg having an upper end and a lower gripping end, wherein the inner leg and outer leg of each pair of forceps are connected together adjacent to their upper ends and define a gripper at their lower ends, the lower gripping ends of said inner and outer legs of each pair of forceps being movable relative to each other within a plane of motion;
   a connection joining together the inner legs of the first and second pairs of forceps in an orientation such that both pairs of forceps operate in the same plane of motion, which extends through the gripping ends of both pairs of forceps, wherein there is a space between the upper ends of the inner legs through which a user may insert a forefinger.

2. A gripper as recited in claim 1, wherein said connection is adjacent to the lower ends of said inner legs, and further comprising a spacer mounted on said inner legs above said connection to hold the inner legs apart above the connection.

3. A gripper as recited in claim 2, wherein said spacer includes a ring fixed to both of said inner legs.

4. A gripper as recited in claim 1, wherein said connection is a spacer, holding said inner legs apart.

5. A gripper as recited in claim 4, wherein said inner legs are further connected together adjacent their gripper ends.

6. A gripper, comprising:
   first and second pairs of forceps, each pair of forceps including inner and outer legs; a hinge joint connecting together said inner and outer legs, said hinge joint restricting the relative motion between the inner and outer legs to motion within a plane, and each of said inner and outer legs defining a lower, gripping end, wherein the gripping end of each outer leg is movable inwardly, toward the gripping end of its respective inner leg within said plane of relative motion; and
   a spacer connected to the inner legs of said first and second pairs of forceps above their gripping ends, said spacer holding said inner legs apart a fixed distance and holding said pairs of forceps in an orientation such that both pairs of forceps have the same plane of relative motion.

7. A gripper as recited in claim 6, wherein said inner legs are also joined together at a connecting point adjacent their gripping ends.

8. A gripper as recited in claim 7, wherein said spacer includes a ring secured to both of said inner legs.

9. A gripper as recited in claim 7, wherein said spacer holds the inner legs apart approximately the width of a human forefinger.

10. A gripper, comprising
    first and second pairs of forceps, each pair including an inner leg and an outer leg, each of said legs including an upper end and a gripper end;
    a connection fixing the inner legs of said first and second pairs of forceps relative to each other adjacent to their gripper ends so that the inner legs lie between the outer legs; wherein the upper ends of said inner legs are spaced apart approximately the distance of a human forefinger.

11. A gripper as recited in claim 10, and further comprising a spacer mounted on the inner legs above said connection so as to maintain a fixed spacing between said inner legs.

12. A gripper as recited in claim 11, wherein the legs of each pair of forceps are movable relative to each other in a plane of motion, and wherein said connection orients said first and second pairs of forceps relative to each other so that they both operate in the same plane of motion.

* * * * *

UNITED STATES PATENT AND TRADEMARK OFFICE
CERTIFICATE OF CORRECTION

PATENT NO. : 6,863,679 B1
DATED : March 8, 2005
INVENTOR(S) : William Stephen Aaron It is certified that error appears in the above-identified patent and that said Letters Patent is hereby corrected as shown below:

Column 1,
Line 62, delete the word "is".

Column 2,
Line 26, delete "fore" and insert therefor -- force --.

Signed and Sealed this

Seventeenth Day of May, 2005

JON W. DUDAS
*Director of the United States Patent and Trademark Office*